US 6,587,733 B1

(12) United States Patent
Cross, Jr. et al.

(10) Patent No.: US 6,587,733 B1
(45) Date of Patent: Jul. 1, 2003

(54) PERCUTANEOUS SURGICAL LEAD BODY WITH DIRECTED STIMULATION

(75) Inventors: Thomas E. Cross, Jr., St. Francis, MN (US); Vladimir Redko, Houston, TX (US); Kenneth M. Alo, Bellair, TX (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 09/500,201

(22) Filed: Feb. 8, 2000

(51) Int. Cl.[7] ................................................. A61N 1/05
(52) U.S. Cl. ...................... 607/116; 607/117; 607/148; 600/393
(58) Field of Search ................................ 604/116, 117, 604/121–123, 148; 600/373, 377, 393

(56) References Cited

U.S. PATENT DOCUMENTS

| | | | |
|---|---|---|---|
| 5,697,951 A | 12/1997 | Harpstead et al. | ............. 607/3 |
| 5,702,437 A | 12/1997 | Baudino | .................... 607/116 |
| 5,713,923 A | 2/1998 | Ward et al. | .................... 607/3 |
| 5,865,843 A | 2/1999 | Baudino | .................... 607/116 |
| 5,895,416 A | 4/1999 | Barreras, Sr. et al. | |
| 5,913,882 A | 6/1999 | King | ............................. 607/62 |
| 6,141,594 A | * 10/2000 | Flynn et al. | ................. 600/374 |
| 6,205,361 B1 | * 3/2001 | Kuzma et al. | ............... 607/116 |
| 6,212,434 B1 | * 4/2001 | Scheiner et al. | ............ 607/123 |

FOREIGN PATENT DOCUMENTS

| | | |
|---|---|---|
| EP | 0 580 928 A1 | 2/1994 |
| EP | 0 862 925 A2 | 9/1998 |
| WO | WO 99/56818 | 11/1999 |

* cited by examiner

Primary Examiner—Kennedy Schaetzle
(74) Attorney, Agent, or Firm—Banner & Witcoff, Ltd.

(57) ABSTRACT

There is disclosed a surgical lead comprising two percutaneous lead bodies bonded together. The inventive lead body results in the equivalent of a surgical lead body with columns of electrodes either adjacent to or offset from each other. A bridge of urethane material is used to bond together the percutaneous lead bodies and still provide suitable flexibility of the lead. The surface of the electrodes may be coated, in part, with a suitable non-conductive coating to effectively direct the electrical stimulation signals toward the targeted stimulation area. Significantly, the resulting lead is sized to fit within a needle having a similar cross-section, thereby permitting the percutaneous implantation of the inventive lead.

24 Claims, 1 Drawing Sheet

PERCUTANEOUS SURGICAL LEAD BODY WITH DIRECTED STIMULATION

BACKGROUND OF THE INVENTION

1. Field of the Invention

The present invention relates to surgical lead bodies which provide electrical stimulation to nerve tissue of a patient. More particularly, but without restriction to the particular use which is shown and described, the present invention relates to a surgical lead body having a minimum cross section such that the surgical lead body may be percutaneously implanted through a modified Tuohy needle having an oblong shaped opening.

2. Description of the Related Art

It is known that nerve tissue stimulation is used to treat numerous neurological disorders, including, but not limited to, cerebral palsy, multiple sclerosis, amyotrophic lateral sclerosis, dystonia, and torticollis. It is further known that nerve tissue stimulation is useful to treat intractable malignant and nonmalignant pain. Stimulation of nerve tissue of the spinal cord, for example, is often accomplished through implanted medical leads in the epidural space of the spinal cavity. The implanted lead defines a lead body which includes neural stimulation electrodes that conduct electrical stimulation signals from a stimulation source, such as implantable pulse generators, to targeted nerve fibers in the epidural space. These medical leads may be percutaneous lead bodies which have a cylindrical shape with cylindrical electrodes spaced along the body of the lead. Also, the medical leads may be surgical lead bodies with electrodes spaced in an array on a paddle-type lead body.

As conventional, the percutaneous lead body is introduced into the epidural space of the spinal cord using a needle and stylet. The needle (commonly referred to as a Tuohy needle) and stylet are interested into the targeted spinal column area between adjacent vertebrae until the tip of the needle and stylet are positioned into the epidural space. The stylet is withdrawn and a percutaneous lead body is inserted through the opening or lumen of the needle into the epidural space and positioned at the targeted stimulation area. The needle is then withdrawn leaving the percutaneous lead body in the desired stimulation position. Drawbacks encountered with known percutaneous lead bodies include migration or movement of the lead body after it is implanted. In addition, the cyclindrical shape of the electrode in the percutaneous lead body generates omni-directional stimulation instead of one-directional, focused stimulation.

The surgical lead body which is typically a paddle-type lead body often has a rectangular, flat cross-section. Spaced in an array on one side of the paddle are the electrodes. The array of electrodes provides better stimulation coverage of the targeted nerve tissue than a percutaneous lead body. In contrast to the percutaneous lead body, however, the surgical lead body is surgically implanted into the epidural space. This requires a physician to perform a laminotomy, laminectomy, or similar procedure, prior to the insertion of the surgical lead into the epidural space. Once implanted, the surgical lead having the flat, rectangular shape is generally more stable than a percutaneous lead and provides one-directional stimulation—stimulation more focused than a percutaneous lead body. A drawback with the surgical lead body, however, is the performance of a laminotomy or similar surgical procedure. Anesthesiologists who frequently provide the nerve tissue stimulation for a patient are often prevented from using the surgical lead body as the laminotomy procedure is generally outside the scope of their practice.

SUMMARY OF THE INVENTION

Accordingly, it is an object of the present invention to provide an implantable lead body that provides the advantages of the surgical lead body but does not require performing a laminotomy, or other surgical procedure, prior to implantation. It is another object of the present invention to provide a lead body that may be percutaneously implanted at the targeted nerve tissue. It is yet another object to provide a lead body having the stability of a surgical lead. Another object is to provide a lead body having an array of spaced electrodes for better stimulation coverage of the targeted nerve tissue. Still another object of the present invention is to provide a lead body having one-directional, focused stimulation.

Briefly, in summary, the present invention comprises bonding together two percutaneous lead bodies, resulting in the functional equivalent of a surgical lead body. The inventive medical lead body forms columns of electrodes which are either adjacent to or offset from each other, thus forming an array of electrodes. The bonding of the percutaneous lead bodies is accomplished by a plurality of urethane bridges molded to each of the percutaneous lead bodies. The plurality of bridges provides structural integrity to the medical lead yet permits the desired flexibility of the lead body. One side of the inventive medical lead body is "masked" or coated with a suitable non-conductive material. The masking of one side of the medical lead body makes that side of the lead body non-conductive and effectively directs the stimulation signals transmitting from the cylindrical electrodes toward the desired stimulated area for focused stimulation. In contrast to the surgical lead body, the medical lead body of the present invention may be percutaneously implanted. The percutaneous implantation is achieved by inserting the inventive medical lead body through a modified Tuohy needle having an oblong cross-section or other similar needle, such as, the needle disclosed in U.S. patent application Ser. No. 09/303,045, now U.S. Pat. No. 6,249,707 which is incorporated herein by reference.

Examples of the more important features of this invention have been broadly outlined above in order that the detailed description which follows may be better understood and so that contributions which this invention provide to the art may be better appreciated. There are, of course, additional features of the invention which will be described herein and which will be included within the subject matter of the claims appended hereto.

BRIEF DESCRIPTION OF THE DRAWINGS

The preferred embodiments of the invention will be described in relation to the accompanying drawings. In the drawings, the following figures have the following general nature.

In the accompanying drawings, like reference numbers are used throughout the various figures for identical structures.

DESCRIPTION OF THE PREFERRED EMBODIMENTS

Figure 1:
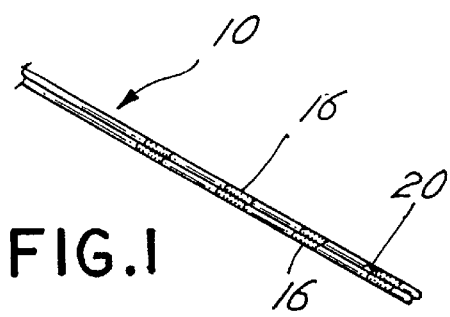
FIG. 1 is an isometric view of the surgical lead of the present invention.
Figure 2:
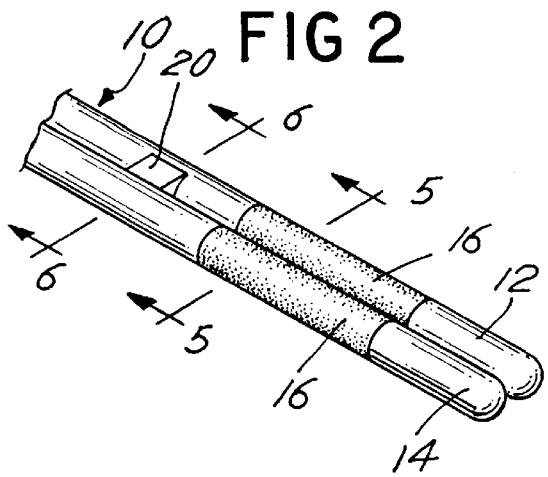
FIG. 2 is an enlarged isometric view of the lead of FIG. 1 illustrating the position of the electrodes and the urethane bridge.

Referring to FIGS. 1 and 2, there is disclosed a preferred embodiment of the medical lead 10 of the present invention useful for spinal cord, deep brain and peripheral nerve stimulation. The inventive medical lead 10 has a sufficiently small cross-section so as to permit percutaneous implantation of the lead at a targeted stimulation area via a modified Tuohy needle having an oblong cross-section. Significantly, the medical lead 10 provides the advantages of a surgical paddle-type lead, such as, better stimulation coverage and improved stability, without a physician or anesthesiologist having to perform a laminotomy or other similar surgical procedure to implant the medical lead.

As depicted in the figures, the medical lead 10 includes a pair of percutaneous lead bodies 12, 14 which are joined together in parallel relation along the edges of each lead. Note that the lead bodies 12, 14 may be molded as a one-piece body depending on desired rigidity of the lead 10, more fully discussed below. As conventional, each of the lead bodies 12, 14 define a cylindrical lead body and a round end. The lead body is made from polyurethane or other suitable material. Spaced along each of the lead bodies 12, 14 is at least one electrode 16 to provide electrical stimulation to the targeted nerve tissue. Each electrode is typically cylindrical in shape and thus provides stimulation in all directions away from the lead body. It should be understood that other shapes and types of electrodes may be used with the present invention and still be considered to be within the scope of the same. Each of the lead bodies 12, 14 further include at least one wire conductor, not shown, connected to the electrodes. As conventional, each wire conductor of the lead bodies 12, 14 may be coupled to an implantable neurological pulse generator, additional, intermediate wiring, or other stimulation device. The stimulation pulses produced by the implantable neurological pulse generator or other stimulation device are carried from the pulse generator through the wire conductors to the electrodes in each lead body 12, 14 and out to the targeted tissue. The plurality of electrodes permits varying stimulation of the targeted area. That is, one or more of the electrodes on the lead bodies 12, 14 transmit the stimulation pulses to targeted human tissue depending on the desired stimulation.

As depicted, the percutaneous lead bodies 12, 14 are joined in parallel relation and bonded together by a urethane material, such as polyurethane or other suitable material. The bonding is preferably achieved by a plurality of urethane bridges 20 spaced along the lead bodies. It should be noted that other attachments or means for bonding the lead bodies may be used with the present invention. The preferred urethane bridges 20 are molded to the lead bodies 12, 14 through a heating process not pertinent to the present invention. The spaced apart location of the bridges 20 creates a sufficiently rigid lead assembly that may be inserted through the needle and yet is flexible for enhanced positioning at the targeted area for effective stimulation coverage. The number and location of the urethane bridges will vary depending on the desired rigidity or flexibility of the medical lead 10 and these variations are considered to be within the scope of the present invention. Note that the percutaneous lead bodies 12, 14 may be molded as a single lead, thereby effectively creating a single, continuous urethane bridge between the lead bodies, a bridge extending the full length of the lead bodies 12, 14.

Figure 5:
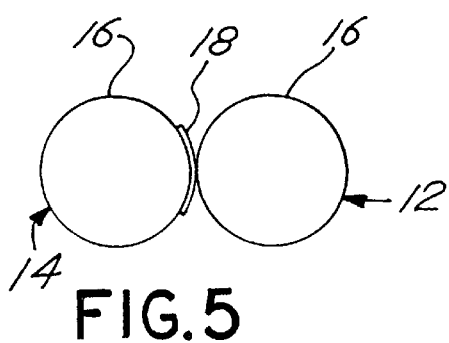
FIG. 5 is an enlarged cross-section view of FIG. 2 taken at line 5—5 illustrating a possible location of the non-conductive coating.
Figure 6:
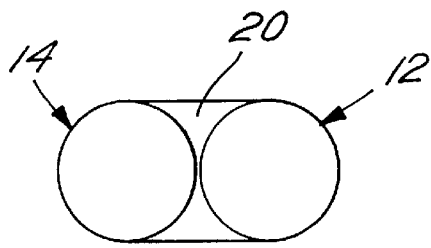
FIG. 6 is an enlarged cross-section view of FIG. 2 taken at line 6—6 illustrating the urethane bridge.

As illustrated in FIG. 2, there is shown one embodiment of the positioning of the percutaneous lead body 12 relative to the percutaneous lead body 14 for controlled orientation of the electrodes 16 of the lead bodies. As depicted, the electrodes 16 on lead body 12 are positioned substantially adjacent to the electrodes 16 on lead body 14. Adjacent electrodes may be in contact with each other or may be spaced apart from each other. Note that the contacting electrodes may be in physical contact with each other but not in electrical contact due to masking of one of the electrodes between the adjacent electrodes, as exemplified in FIG. 5. The lead bodies 12, 14 carrying the contacting electrodes may be connected to each other via one or more urethane bridges. Alternatively, the lead bodies may be connected via a single continuous urethane bridge, as described above. In the same manner, the lead bodies 12, 14 carrying the spaced apart electrodes may be connected to each other via either one or more urethane bridges or a single continuous bridge.

Figure 3:
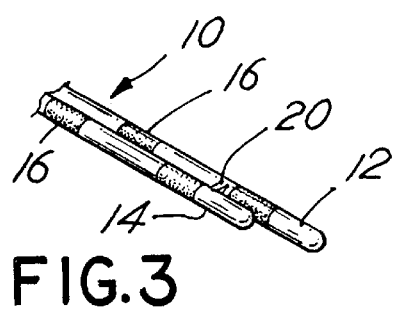
FIG. 3 is an enlarged isometric view of an alternative embodiment of the lead of FIG. 1.

Alternatively, as shown in FIG. 3, the lead bodies 12, 14 may be positioned such that the electrodes 16 are off-set or staggered relative to each other. Again, the urethane bridges are positioned between the electrodes. Depending on the desired rigidity of the lead 10, the embodiment of staggered electrodes creates a more rigid structure than the embodiment where the electrodes are positioned adjacent to each other. As stated above, the number and location of the urethane bridges further affects the rigidity of the lead 10. In either embodiment, however, the electrodes form an array and are spaced both laterally and longitudinally from each, similar to a surgical paddle-type lead. This array provides the advantages of the surgical lead, namely, stimulation coverage of a larger targeted area and varying stimulation of the nerve tissue.

Figure 4:
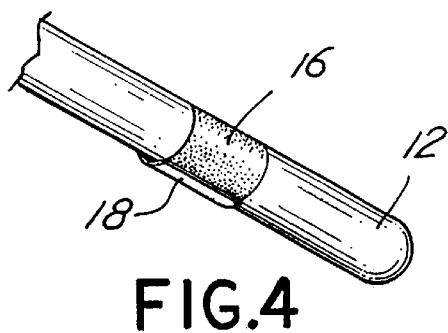
FIG. 4 is an enlarged isometric view of one of the percutaneous lead bodies of FIG. 1 illustrating a possible location of the non-conductive coating (the coating is slightly removed for clarity).
Figure 7:
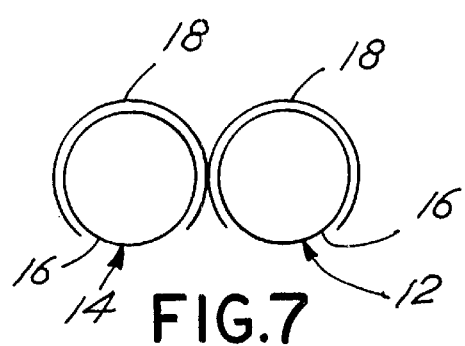
FIG. 7 is an enlarged cross-section view of FIG. 2 taken at line 5—5 illustrating an alternative location and application of the non-conductive coating (the coating is slightly removed for clarity).

The medical lead 10 of the present invention defines two sides. As exemplified in FIG. 4, applied to either of the sides is a non-conductive coating 18, preferably a polyurethane, parylene, or similar type coating or paint. The non-conductive coating applied to a portion of the medical lead 10, and specifically the electrode, renders that surface non-conductive. This has the effect of directing the stimulation signal toward the conductive side—the side opposite the coated side—for focused stimulation. Significantly, by coating one side of the medical lead 10 to focus the electrical signal, the lead functions in a manner similar to the surgical paddle-type lead where the electrical signal is transmitted in only one direction. It should be understood that depending on the desired stimulation, the amount of coating and the electrode area covered by the coating may vary, as exemplified in FIG. 7. In operation, the medical lead 10 is implanted with the non-coated side of the medical lead 10 placed adjacent to the targeted tissue.

The preferred embodiments of the invention are now described so as to enable a person of ordinary skill in the art to make and use the same. Variations of the preferred embodiments are possible without being outside the scope of the present invention. As an example, one or more percutaneous lead bodies may be bonded to either of the percutaneous lead bodies 12, 14. These additional lead bodies may be bonded in a manner similar to the bonding described above. Alternatively, a third percutaneous lead body may be percutaneously positioned alongside the bonded lead bodies 12, 14 and may be used to provide electrical stimulation similar to that taught by the Holsheimer model disclosed in U.S. Pat. Nos. 5,501,703 and 5,643,330, both owned by Medtronic, Inc. of Minneapolis, Minn., and both incorporated herein by reference. Therefore, to particularly point out and distinctly claim the subject matter regarded as the invention, the following claims conclude the specification.

What is claimed is:

1. A controlled orientation stimulation lead for percutaneous implantation, comprising:
    a first lead body having at least one electrode extending around the periphery of the first lead body;
    a second lead body attached to the first lead body, the second lead body having at least one electrode extending around the periphery of the second lead body;
    a mask applied to a portion of the at least one electrode of either the first or second lead body;
    a first lead side formed from the first lead body attached to the second lead body, the first lead side having a first stimulation pattern; and
    a second lead side opposite the first lead side having a second stimulation pattern that is orientatable to a preselected stimulation site.

2. The controlled orientation stimulation lead as in claim 1 wherein at least one electrode on the first lead body is substantially adjacent to at least one electrode on the second lead body.

3. The controlled orientation stimulation lead as in claim 1 wherein the mask configures the stimulation pattern of the electrode.

4. The controlled orientation stimulation lead as in claim 1 wherein the mask electrically insulates at least one electrode on a first lead body from at least one electrode on a second lead body.

5. The controlled orientation stimulation lead as in claim 1 wherein stimulation lead stiffness is controlled by attachments between the first lead body and the second lead body.

6. An implantable medical lead for electrical stimulation at a targeted stimulation area, the medical lead defining a first and second side, comprising:
    a first percutaneous lead body having at least one electrode,
    a second percutaneous lead body bonded to the first percutaneous lead body, the second percutaneous lead body also having at least one electrode, and
    a non-conductive coating applied to at least a portion of either of the first or second sides of the medical lead,
    whereby the medical lead may be percutaneously implanted at the targeted stimulation area.

7. The implantable medical lead of claim 6 wherein the first and second percutaneous lead bodies are bonded together by a urethane material.

8. The implantable medical lead of claim 7 wherein the bonding of the first and second percutaneous lead bodies is effected by multiple bridges of the urethane material.

9. The implantable medical lead of claim 6 wherein the at least one electrode of the first percutaneous lead body is positioned off-set to the at least one electrode of the second percutaneous lead body.

10. The implantable medical lead of claim 6 wherein the first and second percutaneous lead bodies are bonded together by a continuous urethane bridge.

11. The implantable medical lead of claim 6 wherein the non-conductive coating is polyurethane.

12. A method of forming a surgical lead body comprising the steps of:
    providing a first percutaneous lead body having at least one electrode,
    providing a second percutaneous lead body having at least one electrode,
    bonding the first percutaneous lead body to the second percutaneous lead body to form the surgical lead body, the surgical lead body defining a first side and a second side, and
    coating either of the first or second side of the surgical lead body with a urethane material,
    whereby the surgical lead body may be percutaneously implanted.

13. The method of claim 12 wherein the bonding of the first and second percutaneous lead bodies is accomplished by a plurality of urethane bridges molded to the percutaneous lead bodies.

14. The method of claim 12 further comprising the step of positioning the plurality of electrodes on the first percutaneous lead body adjacent to the plurality of electrodes on the second percutaneous lead body prior to bonding.

15. A method of implanting a surgical lead body comprising the steps of:
    providing a first percutaneous lead body having at least one electrode,
    providing a second percutaneous lead body having at least one electrode,
    bonding the first percutaneous lead body to the second percutaneous lead body to form the surgical lead body, the surgical lead body defining a first side and a second side,
    coating either of the first or second side of the surgical lead body with a urethane material,
    inserting a needle having an opening to a targeted stimulation area,
    inserting the surgical lead body through the opening of the needle to the targeted stimulation area, and
    removing the needle from the targeted stimulation area.

16. The method of claim 15 further comprising the step of inserting the surgical lead body such that the side other than the first or second side having the coating is adjacent to the targeted stimulation area.

17. The method of claim 15 further comprising the step of positioning the at least one electrode on the first and second percutaneous lead bodies off-set to each other prior to bonding.

18. The method of claim 15 wherein the bonding of the first and second percutaneous lead bodies is accomplished by a plurality of urethane bridges molded to the percutaneous lead bodies.

19. The method of claim 15 further comprising the step of positioning the at least one electrode on the first and second percutaneous lead bodies adjacent to each other prior to bonding.

20. An implantable medical lead for electrical stimulation at a targeted stimulation area, the medical lead defining a first and second side, comprising:

a first lead body having at least one electrode, a second lead body bonded at multiple locations to the first lead body, the second lead body also having at least one electrode, and a non-conductive coating applied to at least a portion of either of the first or second sides of the medical lead, whereby the medical lead may be percutaneously implanted at the targeted stimulation area.

21. The implantable medical lead of claim 20 wherein the first and second lead bodies are bonded together by a urethane material.

22. The implantable medical lead of claim 21 wherein the at least one electrode of the first lead body is positioned off-set to the at least one electrode of the second lead body.

23. The implantable medical lead of claim 20 wherein the multiple bonding of the first and second lead bodies is effected by multiple bridges of the urethane material.

24. The implantable medical lead of claim 20 wherein the non-conductive coating is polyurethane.

* * * * *